US009427138B2

(12) United States Patent
Intoccia, Jr. et al.

(10) Patent No.: US 9,427,138 B2
(45) Date of Patent: Aug. 30, 2016

(54) ACCESS DEVICES AND RELATED METHODS OF USE

(71) Applicants: Alfred P. Intoccia, Jr., Nashua, NH (US); Jianmin Li, Lexington, MA (US); Christopher Oskin, Grafton, MA (US)

(72) Inventors: Alfred P. Intoccia, Jr., Nashua, NH (US); Jianmin Li, Lexington, MA (US); Christopher Oskin, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 595 days.

(21) Appl. No.: 13/622,777

(22) Filed: Sep. 19, 2012

(65) Prior Publication Data

US 2014/0081080 A1    Mar. 20, 2014

Related U.S. Application Data

(60) Provisional application No. 61/536,862, filed on Sep. 20, 2011.

(51) Int. Cl.
*A61B 1/00* (2006.01)
*A61B 1/06* (2006.01)
*A61B 1/018* (2006.01)

(52) U.S. Cl.
CPC ............ *A61B 1/00135* (2013.01); *A61B 1/018* (2013.01)

(58) Field of Classification Search
CPC .......... A61B 1/00073; A61B 1/00128; A61B 1/0014; A61B 1/00147; A61B 1/00154; A61B 1/012; A61B 1/0125; A61B 1/018; A61B 2017/003; A61B 2017/3445
USPC .......... 600/128, 140, 112–114, 146, 160, 178
See application file for complete search history.

(56) References Cited

U.S. PATENT DOCUMENTS

| | | | |
|---|---|---|---|
| RE32,158 E * | 5/1986 | Vukovic | 600/123 |
| 5,836,867 A * | 11/1998 | Speier et al. | 600/112 |
| 6,471,639 B2 * | 10/2002 | Rudischhauser et al. | 600/128 |
| 6,827,710 B1 * | 12/2004 | Mooney et al. | 604/500 |
| 6,878,106 B1 * | 4/2005 | Herrmann | 600/104 |
| 7,846,107 B2 * | 12/2010 | Hoffman et al. | 600/561 |
| 7,850,675 B2 * | 12/2010 | Bell et al. | 604/523 |
| 8,314,406 B2 * | 11/2012 | Ntziachristos et al. | 250/458.1 |
| 8,413,659 B2 * | 4/2013 | Crumback et al. | 128/207.14 |
| 8,715,270 B2 * | 5/2014 | Weitzner et al. | 606/1 |
| 2004/0230096 A1 * | 11/2004 | Stefanchik et al. | 600/106 |

(Continued)

OTHER PUBLICATIONS

International Search Report for International Application No. PCT/US2012/056090, mailed Mar. 28, 2013, 2 pgs.

*Primary Examiner* — John P Leubecker
*Assistant Examiner* — Arnaldo Torres Diaz
(74) *Attorney, Agent, or Firm* — Bookoff McAndrews, PLLC (57) ABSTRACT

A system for accessing a patient's body may include an elongate member having a proximal end, a distal end, and two lumens. The elongate member may include two lumens and a thickness of material extending between external and internal surfaces of the elongate member. The system may also include a first illumination device associated with a first of the two lumens such that a portion of the first illumination device may extend into the thickness of material. A second illumination device may be associated with the second of the two lumens such that a portion of the second illumination device may extend into the thickness of material. Further, the system may include an imaging device having a first portion extending into the thickness of material, a second portion protruding into the first of the two lumens, and a third portion protruding into the second of the two lumens.

17 Claims, 5 Drawing Sheets

(56) References Cited

U.S. PATENT DOCUMENTS

| | | | |
|---|---|---|---|
| 2005/0085694 A1* | 4/2005 | Nakao | 600/153 |
| 2005/0203341 A1* | 9/2005 | Welker et al. | 600/130 |
| 2006/0025650 A1 | 2/2006 | Gavriely | |
| 2006/0206004 A1* | 9/2006 | Dehmel et al. | 600/128 |
| 2006/0235269 A1* | 10/2006 | Waxman | 600/104 |
| 2007/0066869 A1 | 3/2007 | Hoffman | |
| 2007/0106113 A1* | 5/2007 | Ravo | 600/113 |
| 2007/0142709 A1* | 6/2007 | Martone et al. | 600/121 |
| 2007/0225559 A1* | 9/2007 | Clerc et al. | 600/117 |
| 2009/0030277 A1* | 1/2009 | Fujimoto et al. | 600/114 |
| 2009/0259103 A1* | 10/2009 | Hirata | 600/114 |
| 2010/0152537 A1* | 6/2010 | Kobayashi | 600/115 |
| 2010/0160729 A1* | 6/2010 | Smith et al. | 600/114 |
| 2010/0198012 A1* | 8/2010 | Poole et al. | 600/115 |
| 2010/0256446 A1* | 10/2010 | Raju | 600/114 |
| 2010/0261962 A1* | 10/2010 | Friedberg | 600/114 |
| 2010/0298642 A1* | 11/2010 | Trusty et al. | 600/114 |
| 2011/0124960 A1 | 5/2011 | St. Onge et al. | |
| 2011/0207999 A1* | 8/2011 | Torisawa et al. | 600/114 |
| 2013/0072754 A1* | 3/2013 | Okamoto et al. | 600/109 |
| 2013/0172670 A1* | 7/2013 | Levy et al. | 600/103 |
| 2013/0225926 A1* | 8/2013 | Smith et al. | 600/114 |

* cited by examiner

ACCESS DEVICES AND RELATED METHODS OF USE

CROSS-REFERENCE TO RELATED APPLICATIONS

This patent application claims the benefits of priority under 35 U.S.C. §§119-120 to U.S. Provisional Application No. 61/536,862, filed on Sep. 20, 2011, the entirety of which is incorporated herein by reference.

FIELD OF THE INVENTION

This disclosure relates generally to systems and methods for medical devices. More particularly, embodiments of the present disclosure relate to medical devices for accessing portions of a patient's body.

BACKGROUND OF THE INVENTION

A wide variety of diagnostic or therapeutic procedures involve introducing an access device into a patient's body. The access device provides an access lumen, which is used to introduce diagnostic or therapeutic instruments into the patient. A general objective of such access devices is to minimize the cross-sectional area of the access lumen while maximizing the available space for the diagnostic or therapeutic instrumentation.

One exemplary environment where access devices are used is the urinary tract of a patient. Access devices are introduced into the urinary tract to perform, e.g., ureteroscopy, including stone extraction, stricture treatment, or stent placement. To remove bladder stones, e.g., a cystoscope is often placed into the bladder through the urethra, and subsequently, access devices such as a ureteral sheath or a catheter are inserted through the cystoscope. These sheaths/catheters, when deployed, provide a working channel for medical devices to access portions of a patient's body to perform desired procedures. For example, a lithotripter and a suction device may be inserted through the catheter to first break-up a urethral stone into smaller pieces and then, extract it from the body.

Those in the art will appreciate that positioning and guidance of such an interventional device may be accomplished by introducing a camera, a light source, or similar devices into the body. Each of these devices may be inserted into the body lumen through working channels in the cystoscope. The sizes of such devices may be limited by the smaller dimensions of a patient's urinary tract. The primary surgical task, such as extracting kidney stones, dictates the tools that must be introduced through the working channels, leaving scant room for auxiliary devices such as cameras and light sources.

Therefore, there exists a need for an improved access device that includes visualization devices while maintaining a substantial cross-sectional area to allow passage of suitable surgical tools.

SUMMARY OF THE INVENTION

Embodiments of the present disclosure provide a system for accessing a location within a patient's body.

In accordance with an aspect of the present disclosure, the system may include an elongate member having a proximal end, a distal end, and two lumens extending therebetween. The elongate member includes an external surface, an internal surface that surrounds the two lumens, and a thickness of material extending between the external and internal surfaces. The system also includes a first illumination device associated with a first of the two lumens. A portion of the first illumination device may extend into the thickness of material and the remaining portion may protrude into the first of the two lumens. A second illumination device may be associated with the second of the two lumens such that a portion of the second illumination device may extend into the thickness of material and the remaining portion of the second illumination device may protrude into the second of the two lumens. Further, the system may include an imaging device having a first portion extending into the thickness of material, a second portion protruding into the first of the two lumens, and a third portion protruding into the second of the two lumens.

In various embodiments, the system may include one or more of the following additional features: the imaging and illumination devices may be spaced from one another; a portion of the elongate member may be steerable; the first and second illumination devices may include light sources; the first and second illumination devices may include light guide tubes having light sources at proximal ends of the light guide tubes; the imaging and illumination devices may be fixedly embedded within the thickness of material; the imaging and illumination devices may be slidably received within the thickness of material; the first and second illumination and imaging devices may each be disposed in respective channels and each channel is separated from the respective lumens by an expandable divider; the divider may be configured to collapse so as to not protrude into the respective lumens when the imaging and illumination devices are removed from the respective channels; and the system further includes a surgical tool within the lumen.

According to another embodiment, a device for accessing a patient's body is provided. The device may include an elongate member having a proximal end, a distal end, and a lumen extending therebetween. A portion of a wall of the lumen may include an expandable divider configured to divide a portion of the lumen into two lumens. The device may also include a visualization component configured to advance through the elongate member so as to expand the divider.

In various embodiments, the device may include one or more of the following additional features: the visualization component may include a camera and a light source; the expandable divider may be configured to collapse once the visualization component is removed from the elongate member; the visualization component may be detachably received within the expandable divider; a portion of the elongate member may be steerable; and the device may include a surgical tool within the lumen.

According to another embodiment, a device for accessing a patient's body is provided. The device may include an elongate member having a proximal end, a distal end, and a lumen extending therebetween. The lumen may be defined by an internal wall of the elongate member. A mounting mechanism may be disposed along a length of a portion of the internal wall. The device may further include a visualization component configured to be removably inserted into the lumen. The visualization component may include a mounting attachment configured to releasably couple with the mounting mechanism.

In various embodiments, the device may include one or more of the following additional features: the elongate member may include a steerable access sheath; the visualization component may include a camera and a light source; and the mounting mechanism may include one of rails or a magnet.

Additional objects and advantages of the claimed invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts.

Overview

Embodiments of the present disclosure relate to access devices and related methods of use for accessing a surgical site within a patient's body. The access device assists in performing minimally invasive procedures such as removing bladder stones or other urological tasks. The access device disclosed here not only provides access to the surgical site but it also assists in visualizing the surgical site during the procedure. For convenience, the term "access device" will be used throughout this application. In general, that term encompasses any suitably elongate sheath (e.g., endoscopes, ureteroscopes, cystoscopes, trocars, and the like) capable of both traversing tortuous anatomical lumens and providing a channel for passage of one or more surgical tools.

The access device may include an elongate tubular member having one or more working channels to perform the desired procedure. In addition, the distal end of the elongate member includes visualization and illumination devices such as a camera and a light source, respectively, allowing a surgeon to visually observe the surgical site. The camera and light source may be either permanently integrated or temporarily coupled to the distal end of the access device. Alternatively, these devices may be detachably introduced through a coupling mechanism within the access device.

In the following sections, embodiments of the present disclosure will be described with reference to a procedure to remove stones from a urinary system. It will be understood that this choice is merely exemplary and that the device may be utilized in any other organ, such as the stomach, or any other organ that requires diagnosis or extraction of undesired objects or masses.

Exemplary Embodiments

Figure 1:
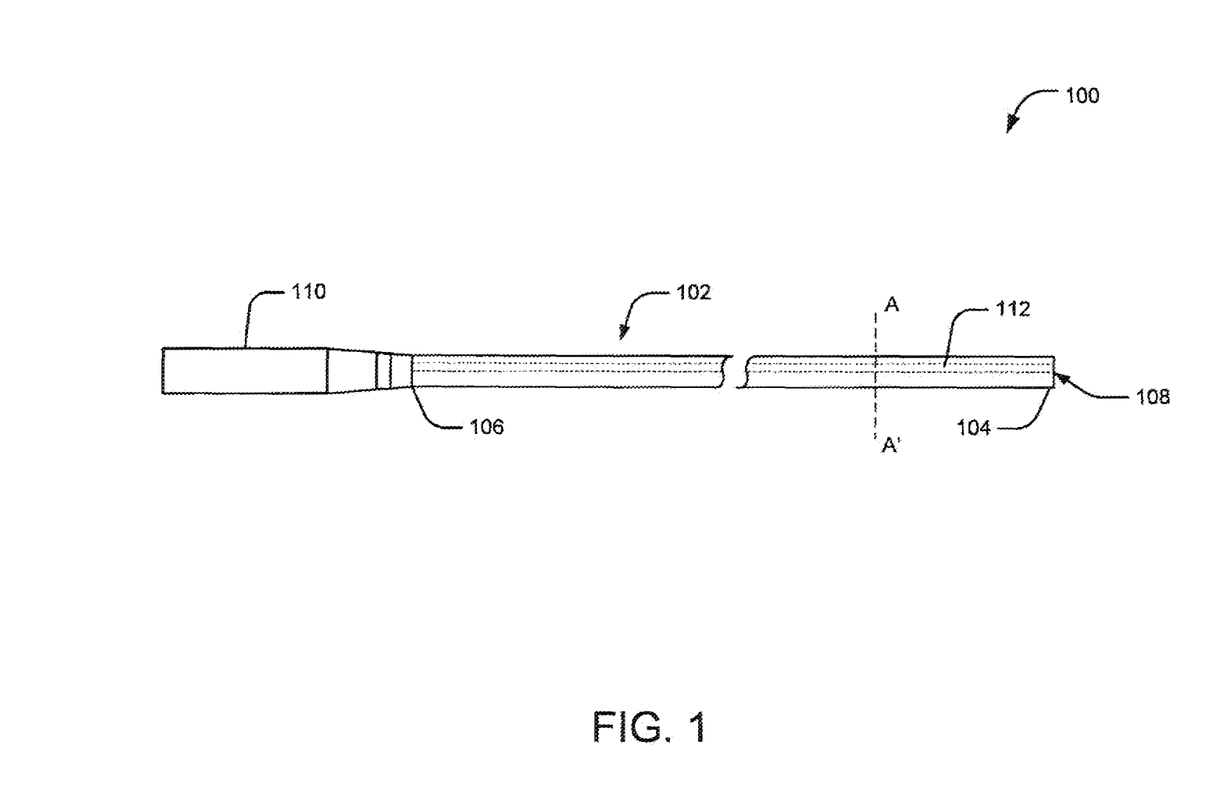
FIG. 1 illustrates an exemplary access device according to an embodiment of the present disclosure.

FIG. 1 illustrates an exemplary access device 100 for accessing a surgical site to perform a desired procedure. The device 100 includes a sheath 102 having a distal end 104, a proximal end 106, and a lumen 108 therebetween. Proximal end 106 may be coupled to a handle 110, while distal end 104 remains open to allow one or devices to extend towards the surgical site. Sheath 102 further includes one or more internal working channels 112 for inserting medical devices into a body.

Sheath 102 is a hollow elongate tube with cross-sectional configuration adapted according to a desired body lumen. In the illustrated embodiment, sheath 102 is generally circular, with a generally circular hollow interior lumen 108. Further, sheath 102 may have a uniform diameter or may be tapered at the distal end to allow convenient insertion within the body. Depending upon the particular implementation and intended use, the length of sheath 102 may vary. The diameter of sheath 102 may be tailored based on the body cavity. Similarly, depending upon the particular implementation and intended use, sheath 102 can be rigid along its entire length, flexible along a portion of its length, or configured for flexure at only certain specified locations.

In one embodiment, sheath 102 may be flexible, adapted for flexible steering within bodily lumens, as understood in the art. For example, sheath 102 can be steered using a steering system (not shown) to move at least a portion (e.g., distal end 104) up/down and/or side-to-side. Additional degrees of freedom, provided for example via rotation, translational movement of sheath 102, or additional articulation of bending sections, are also contemplated. Examples of such steering systems may include pulleys, control wires, gearing, and electrical actuators.

Sheath 102 may be formed of any suitable material having sufficient flexibility to traverse body cavities and tracts. Sheath 102 may be an extrusion incorporating a woven, braided components, or braided using synthetic plastics, fiber, or polymers. In an embodiment, sheath 102 may also be formed by laser cutting a metal tube and then reflowing a suitable covering material on an outer surface of the tube. Alternatively, sheath 102 may be rigid or semi-rigid, formed from materials such as stainless steel or the like, including shape memory alloys such as Nitinol, in general, sheath 102 may be made of any suitable material that is compatible with living tissue or a living system. That is, the sheath 102 may be non-toxic or non-injurious, and it should not cause immunological reaction or rejection. Suitable materials may include nitinol, ePTFE, fabric, and suitable nickel and titanium alloys. Those in the art are well aware of the range of suitable and available materials.

In addition, sheath 102 may be self-expandable, or it may expand by some actuation mechanism incorporated in the handle 110. Sheath 102 may be inserted into a patient's body in a collapsed state, and once deployed, it may expand radially, increasing the size of lumen 108. In other embodiments, sheath 102 may be inverted and everted during or after insertion into a patient's body.

Moreover, the sheath 102 may be designed to impose minimum risk to the surrounding tissues while in use. To this end, one or more portions of sheath 102 may include atraumatic geometrical structures, such as rounded or beveled terminal ends or faces, to reduce trauma and irritation to surrounding tissues.

To effectively maneuver the sheath 102 within a body cavity, the operator should know the exact location of the sheath 102 in the body cavity at all times. To this end, one or more portions of the sheath 102 may be radiopaque, such as by inclusion of barium sulfate in plastic material or inclusion of one or more metal portions, which provide sufficient radiopacity. Alternatively, distal end 104 of sheath 102 may include radiopaque or sonoreflective markers (not shown). These markings facilitate detection of a position and/or orientation of the sheath 102 within a patient's body, and a surgeon, with the aid of suitable imaging equipment, may track the path followed by sheath 102 and avoid potential damage to sensitive tissues.

Further, the sheath 102 may include any suitable coating and/or covering. For example, the outer surface may include a layer of lubricous material to facilitate insertion through a body lumen or surgical insertion. Further, sheath 102 may be coated with a biocompatible material such as Teflon. To inhibit bacterial growth in the body cavity, sheath 102 may be coated with an antibacterial coating. Further, an anti-inflammatory substance may also be applied to the outer surface of the sheath 102, if required.

The proximal end 106 of sheath 102 can be coupled to handle 110 for gripping by an operator such as a surgeon, while the distal end 104 remains open for medical devices to extend out. Handle 110 can be attached to sheath 102 by, for example, welding, use of an adhesive, or integrally forming with sheath 102.

The handle portion may include one or more ports to introduce medical devices into the working channels 112 of sheath 102. Further, the handle portion may include an actuating mechanism (not shown) to actuate one or more medical devices at the distal end of sheath 102 or selectively expand sheath 102, as desired. For example, the handle may include an actuating mechanism to power on or off an integrated suction device, illumination device, and/or imaging device.

Sheath 102 may include one or more working channels 112. Through these channels, an operator may introduce one or more medical devices to extend from distal end 104. For example, during prostatectomy, the operator may introduce a suction device and a morcellator device into the working channel 112. Those skilled in the art will understand access devices typically require a camera and light source to view the surgical site during a procedure. Conventionally, these devices are passed through the working channel of the access device, compromising the working space available for required surgical tools and instruments.

To ensure greater working space, embodiments of the present disclosure employ access device 100 with visual capabilities. To this end, the distal end 104 of sheath 102 includes visualization devices such as a camera and a light source. These devices may be integrally formed with the sheath 102 or may attach to the distal end 104 using known coupling mechanisms. Alternatively, the visualization devices may be detachably introduced into sheath 102 from time to time when required. The following sections describe different embodiments of the access device 100 with visual capabilities in connection with FIGS. 2, 3, 4, 5A and 5B.

Figure 2:
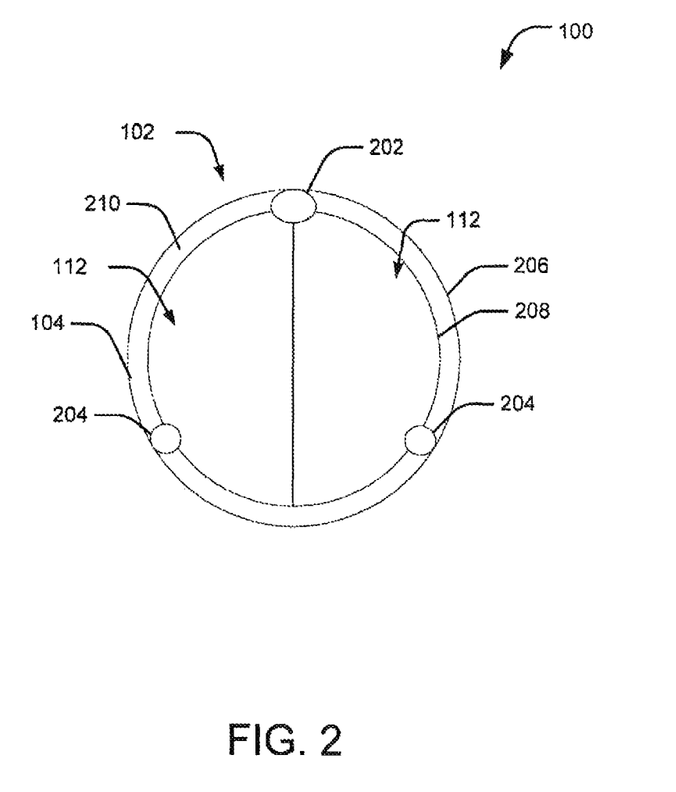
FIG. 2 illustrates an end view of the access device of FIG. 1, showing the distal end of the access device including channels, and visualization and illumination devices.

FIG. 2 illustrates an end view of sheath's 102 distal end 104 depicting channels and visualization devices. As shown, sheath 102 includes two semi-circular shaped working channels 112, and a camera 202 and light sources 204 (combination referred to as "visualization device", hereafter) attached to the distal end 104 of the sheath 102.

In general, working channels 112 can be defined by elongate hollow lumens that extend between proximal end 106 and distal end 104 of sheath 102. While two channels are illustrated, fewer channels or more channels are also contemplated. The number of channels and their configuration can be varied depending on the intended use of the system and the tools required during a procedure. For example, the sheath 102 can include a single channel adapted to receive multiple tools. In such a situation, lumen 108 of sheath 102 may itself act as the working channel 112.

In addition, the distal end of sheath 102 includes spaced apart camera 202 and light sources 204, assisting a surgeon during any surgical procedure. As shown, these visualization devices are mounted on the circumferential distal end surface of sheath 102 such that the devices are embedded within the walls of sheath 102. In general, sheath 102 includes an outer surface 206 and an inner surface 208, and a material thickness 210 extends between the outer and inner surfaces 206, 208. A portion of the visualization devices extend into the thickness 210 and the remaining portion protrude into one or more working channels 112. As shown, a portion of light sources 204 extend into the thickness of sheath and the remaining portion extend into one of the two working channels. Similarly, a portion of camera 202 extends into the sheath 102 and the remaining portion extends into both the working channels 112. The illustrated embodiment depicts one camera device 202 and two light sources 204. It should be understood that the number of devices rooted onto sheath's walls may vary. For example, a single light source may be attached as opposed to two light sources shown in FIG. 2. Alternatively, more than two light sources may be mounted along the circumferential edge of sheath 102 to provide a better view of the surgical site. Similarly, more than one camera device may be integrally provided with sheath 102.

Camera 202 may be an elongate imaging device/system having a display screen (not shown) at the proximal end 106 to present the images captured by the camera. In general, a miniature camera, as small as 1 mm by 1 mm, may be attached to the distal end 104. In addition, these cameras may have approximately 5000 to 100,000 pixel resolution to capture a clear view of the surgical site. Alternatively, a telescope or any known visualization device may replace camera 202 without departing from the scope of the present disclosure. As known in the art, camera 202 may include any suitable image processing capabilities. For example, camera 202 may be configured to capture and present magnified images of target sites.

Light sources 204 may be any known device that illuminates the distal end of the sheath 102 and proximate body structures. For example, an LED light source may be employed. Alternatively, incandescent or fluorescent lamps, nanotechnology diodes, bioflourescent/bioluminescent materials, or other light source known to those in the art may be employed. In the illustrated embodiment, the light sources 204 may include an array of LEDs mounted on the distal end to provide a better view of the surgical site. In an alternate embodiment, light sources 204 may also be light guide tubes, with the light sources attached to the proximal end 106 and the guide tubes transmitting the light to the distal end 104 and beyond. Further, light tubes may also be replaced by laser fibers. In each of the above embodiments, each light source 204 may provide differing intensity, brightness, and color, as desired. In an embodiment, a controller attached to handle 110 may control the functionality of each light source 204 individually.

Camera 202 and light sources 204 may be permanently or temporarily mounted on sheath 102. For a permanent arrangement, these devices may be welded or glued to the thickness of sheath 102. Alternatively, camera 202 and light sources may be made integrally with sheath 102. Otherwise known temporary attachment mechanisms such as snap fit or attachment fit mechanisms may be employed. Facilitating devices, such as grooves, openings, or protrusions may assist in mounting these devices. The visualization devices may be mounted before the sheath is inserted into a patient, and they may remain in place as long as the sheath is in use.

In another embodiment, inner surface 208 of sheath 102 may include separate channels for each visualization device. A portion of these channels may extend into the thickness of sheath 102 and the remaining portion may extend into one of the working channels 112. Further, these channels may be rigid lumens or expandable members that expand into their respective working channels once visualization devices are inserted, and collapse when the visualization devices are retracted.

Camera 202 and light sources 204 may be activated wirelessly or through wired connections. For a wireless connection, these devices may be battery powered and may be connected to a controller attached to handle 110 or proximal end 106. In combination, the resulting system can capture images, and control the amount of illumination. Those skilled in the art will understand that any known wireless connection mechanism, such as Bluetooth, may be employed. For wired connection, however, a set of cables may run along the length of the sheath 102 to connect the visualization devices to a power supply located at the proximal end. These cables may run into the thickness of the sheath 102 to retain the size of working channels 112. In one implementation, a controller may both control the function of the wired devices and also act as a power supply. Alternatively, light sources 204 may be connected to camera 202 for power supply and camera 202 in turn may be connected to an external power supply or a controller, either wirelessly or via cables.

Wired connections may include additional channels running along the length of the sheath 102 to encapsulate the cables. For light sources 204, a set of optical fibers attached to the inner surface of the sheath 102 may allow light to pass through. Optical fiber or channels may run from any position within the sheath 102, however, it should be understood that connecting these channels to the inner surface of sheath 102 may ensure greater working channel space.

In an alternate embodiment, a swivel mechanism may be introduced at the distal end 104. The swivel mechanism allows the distal end 104 containing the camera 202 and light sources 204 to swivel, allowing it to capture each portion of the surgical site effectively. Any conventional swivel mechanism may be used without departing from the scope of the present disclosure. In addition, the distal end 104 of sheath 102 may be selectively steerable to angle distal end 104 at desired surgical sites.

Figure 3:
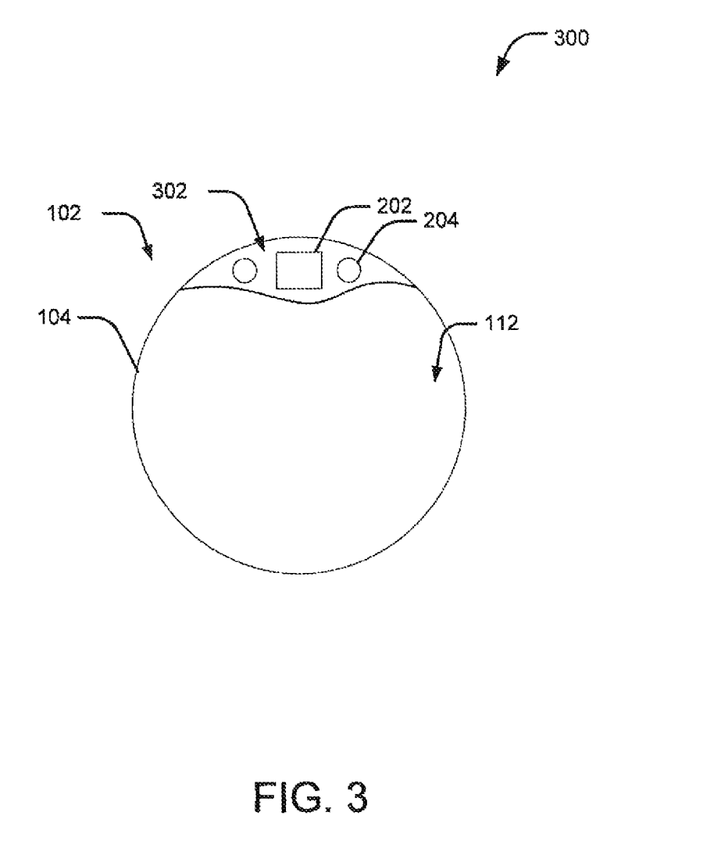
FIG. 3 illustrates another embodiment of the distal end of the access device shown in FIG. 2.

Various alternatives of the access device 100 may be contemplated. FIG. 3 illustrates another exemplary embodiment of an access device 300. As shown, camera 202 and light sources 204 may be integrated into a single visualization device 302, which may be attached to any suitable location along an inner surface of sheath 102. As noted, this visualization device may be permanently or temporarily attached to the sheath 102. For wireless connection, visualization device 302 may be a small-sized device connected to the distal end 104. For wired connections, however, it may be an elongate device running along the length of the sheath 102. The cross-sectional shape of the visualization device 302 may vary from circular, square, rhombic, to any desired shape that may utilize minimum working channel area. Further, the elongate visualization device may be tapered at the distal end or the proximal end. The illustrated configuration in FIG. 3 provides for maximum working lumen dimensions.

Embodiments discussed in FIGS. 2 and 3 illustrate camera and light source devices connected to sheath 102. The present disclosure allows visualization devices to be detachably connected to sheath 102 such that these devices may be retrieved, when not required, to increase the working channel area. The following section describes other embodiments of the access device 100 that facilitate a detachable mechanism in connection with FIGS. 4, 5A and 5B.

Figure 4:
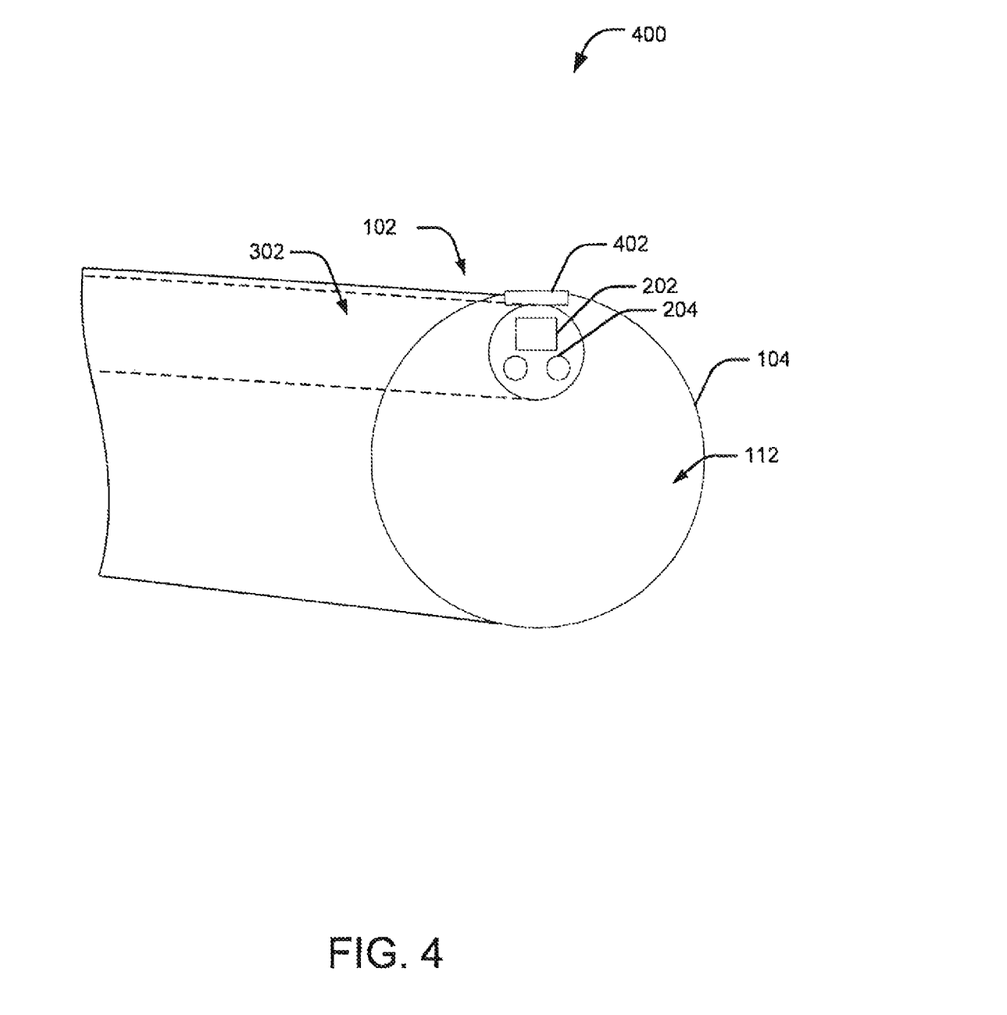
FIG. 4 depicts an embodiment of an access device illustrating a detachable coupling between the access device and the visualization device, according to embodiments of the present disclosure.

FIG. 4 illustrates an embodiment of an access device 400 in which visualization device 302 is attached to sheath 102 through a detachable coupling mechanism 402. Any known detachable mechanism may be employed to allow the visualization device 302 to be inserted into and retrieved from the sheath 102 as desired. For example, coupling mechanism 402 may be a set of rails or slots running completely or partially along the inner surface of the sheath 102, allowing visualization device 302 to traverse on them. Moreover, outer surface of visualization device 302 may include grooves, projections, or similar devices enabling secure movement of visualization device 302 over the rails/slots. The rails or slots may be embedded within the thickness of sheath 102 such that visualization device may be slidably received within the sheath's thickness. Coupling mechanism 402 may also include a magnetic device to temporarily hold visualization device 302, which may also include a metallic distal end or a metallic piece attached to its distal end.

Other coupling mechanisms include snap fit or threaded connections. Alternatively, the distal end of the sheath 102 may include projections (not shown) for securing camera 202 and light sources 204. Further, the projections may be connected to a spring-like device that may push out the projections from the inner sheath surface by pulling a set of wires attached to the spring. If camera 202 and light source 204 are not required, releasing the wires pushes the projections to their retracted state, next to the inner sheath surface. Subsequently, the visualization device 302 may be retrieved easily. Further, the distal end of visualization device 302 and sheath 102 may include threads to screw the two devices together. In the configuration where camera 202 and light sources 204 are inserted through a channel or an optical fiber, the entire channels or fiber may be pulled out of the snap fit or threaded connection. Alternatively, a luer-lock mechanism or other known coupling mechanism may be employed.

Figure 5A:
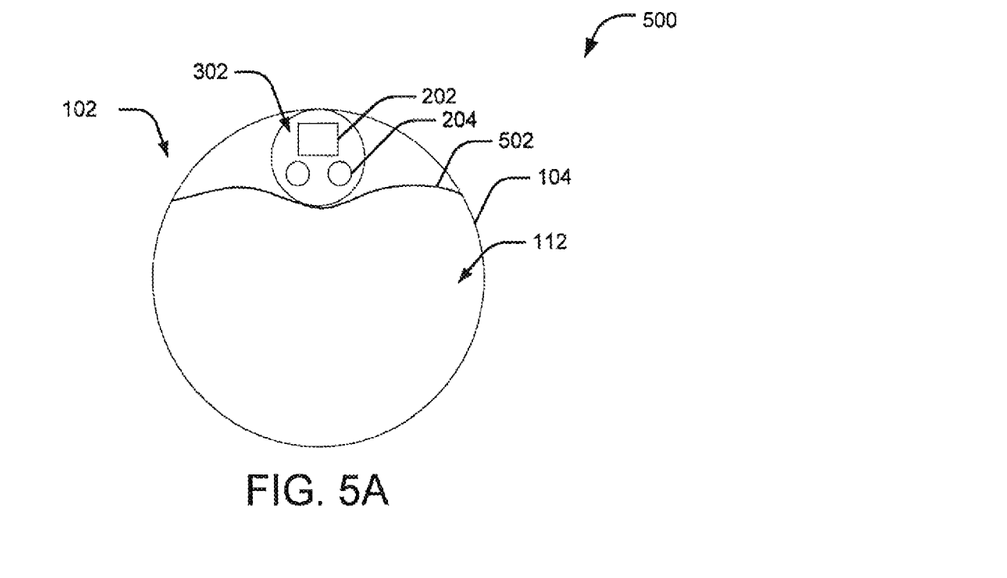
FIGS. 5A and 5B illustrate an alternate embodiment of an access device, according to embodiments of the present disclosure.
Figure 5B:
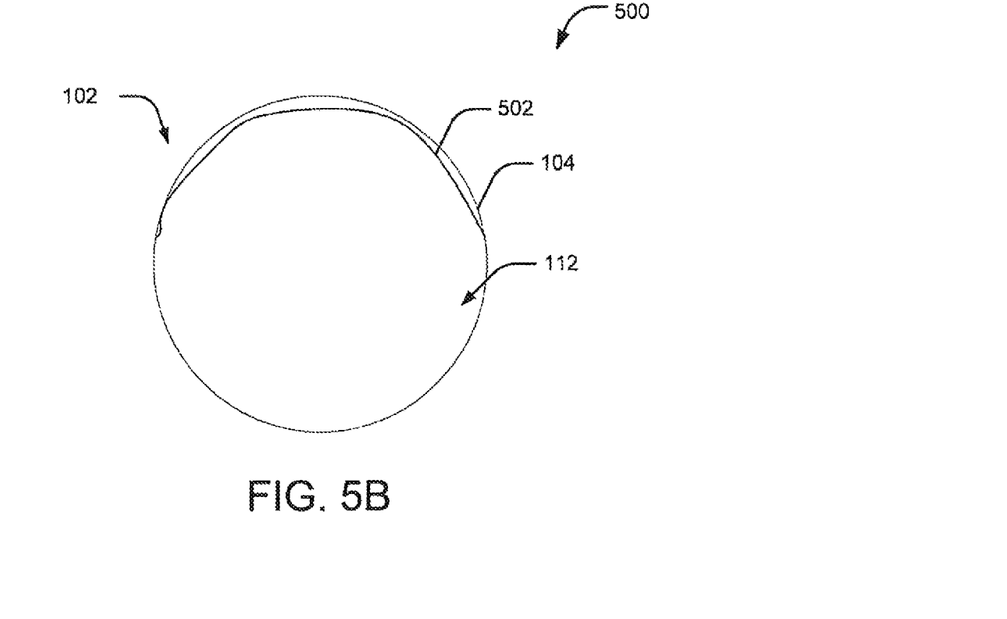

FIGS. 5A and 5B illustrate another embodiment of an access device 500 depicting a detachable connection between sheath 102 and visualization device 302. As shown, sheath 102 includes an expandable divider or pocket 502 attached to the inner surface of sheath 102. In general, pocket 502 may be formed of a flexible membrane, such as rubber, plastic, elastomers, or polymers. When visualization device 302 is not inserted in the sheath 102, pocket 502 may collapse against the inner wall of sheath 102, converting the complete sheath's lumen into working channel 112 as shown in FIG. 5B. When inserted, visualization device 302 may push the pocket 502 away from the inner wall and into the working channel 112, shown in FIG. 5A. When camera 202 is not required, the visualization device 302 may be retracted, and the flexible pocket 502 may return to its original position (against the inner wall), shown in FIG. 5B.

The shape and configuration of pocket 502 may vary. Pocket 502 may extend completely or partially along the length of the sheath 102. Further, pocket 502 may be tapered at the proximal or distal end, based on the cross-sectional shape of the visualization device 302.

Although FIGS. 4, 5A and 5B are discussed with visualization device 302 having camera 202 and light source 204 assembly. Those skilled in the art, however, will understand that each of the embodiments may provide detachable coupling to individual camera 202 and light source 204 as opposed to the assembly.

Embodiments of the present disclosure can be used for a variety of therapeutic procedures such as ureteroscopy, hysteroscopy, or cystoscopy. For example, the access device 100 may be suitable to remove any undesired mass, such as kidney stones or gall bladder stones, or body parts, such as a prostate gland. Alternatively, access device 100 may be used to implement any surgical procedure where an access device needs to be inserted into a small-size bodily lumen, requiring visual capabilities. The following section describes an exemplary method for treating kidney stones.

The access device 100 is inserted into a patient's body until it reaches the kidney. To this end, either a percutaneous incision is made to access the kidney, or the access device 100 may be inserted through a natural opening.

Once inserted, the access device 100 may be maneuvered towards the kidney stone. In use, camera 202 and light sources 204, pre-installed to the distal end of sheath 102, may assist in maneuvering sheath 102 towards the kidney stone. A practitioner may view the surgical site during the procedure. For this purpose, the distal end of sheath 102 may be permanently attached to camera 202 and light source 204. Alternatively, visualization device 302 may be inserted into the sheath 102, when required, through coupling mechanism 402 or flexible pocket 502 within the sheath 102, as discussed in connection with FIGS. 4-5B. Along with the visualization devices, the working channel 112 of sheath 102 may include additional surgical tools such as a laser fiber, a grasper, a basket, a snare, forceps, biopsy jaws, a lithotripter, or other devices assisting in extracting and/or morcellating. These surgical tools may be pre-loaded within sheath 102 permanently or temporarily.

With the help of visualization devices, distal end of sheath 102 is maneuvered proximate the kidney stone, where one or more of the surgical tools can perform the required procedure. In another embodiment, visualization device 302 may be detachably connected to the sheath 102 such that the visualization device 302 may be retracted once the sheath 102 reaches its desired location, providing a larger working channel to perform procedures such as extracting large stone pieces. Also, in some procedures, a surgeon may be required to view the internal body parts only for a limited period of the procedure, and subsequently, the visualization device 302 may be retracted.

Detachable or temporary attachment allows disposing camera 202 after one use or multiple uses. Further, a surgeon may easily sterilize the detachable device to prevent any infection.

Embodiments of the present disclosure may be used in any medical or non-medical procedure, including any medical procedure where monitoring of a body part is required along with a surgical operation. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein, it is intended that the specification and examples be considered as exemplary only, with a true scope and spirit of the invention being indicated by the following claims.

What is claimed is:

1. A system for accessing a location within a body, the system comprising:
    an elongate member having a proximal end, a distal end, and two lumens extending therebetween, wherein the elongate member includes an external surface, an internal surface that surrounds the two lumens, and a thickness of material extending between the external and internal surfaces;
    a first illumination device associated with a first of the two lumens, wherein a portion of the first illumination device extends into the thickness of material and the remaining portion of the first illumination device protrudes into the first of the two lumens;
    a second illumination device associated with the second of the two lumens, wherein a portion of the second illumination device extends into the thickness of material and the remaining portion of the second illumination device protrudes into the second of the two lumens; and
    an imaging device having a first portion extending into the thickness of material, a second portion protruding into the first of the two lumens, and a third portion protruding into the second of the two lumens;
    wherein the first illumination device is disposed in a first channel, the second illumination device is disposed in a second channel, and the imaging device is disposed in a third channel, wherein each of the first channel, the second channel, and the third channel is separated from the respective lumens by an expandable divider.

2. The system of claim 1, wherein the imaging and illumination devices are spaced from one another.

3. The system of claim 1, wherein a portion of the elongate member is steerable.

4. The system of claim 1, wherein the first and second illumination devices include light sources.

5. The system of claim 1, wherein the first and second illumination devices include light guide tubes having light sources at proximal ends of the light guide tubes.

6. The system of claim 1, wherein the imaging and illumination devices are fixedly embedded within the thickness of material.

7. The system for claim 1, wherein the imaging and illumination devices are slidably received within the thickness of material.

8. The system of claim 1, wherein the divider is configured to collapse so as to not protrude into the respective lumens when the imaging and illumination devices are removed from the respective channels.

9. The system of claim 1, further including a surgical tool within the lumen.

10. The system of claim 1, wherein each of the two lumens are axially fixed with respect the elongate member.

11. A system for accessing a location within a body, the system comprising:
    an elongate member having a proximal end, a distal end, and two lumens extending therebetween, wherein the elongate member includes an external surface, an internal surface that surrounds the two lumens, and a thickness of material extending between the external and internal surfaces;

a first illumination device associated with a first of the two lumens, wherein at least a portion of the first illumination device extends into the thickness of material;

a second illumination device associated with the second of the two lumens, wherein at least a portion of the second illumination device extends into the thickness of material; and an imaging device having a first portion extending into the thickness of material;

wherein a portion of the elongated member is steerable; and wherein the first illumination device is disposed in a first channel, the second illumination device is disposed in a second channel, and the imaging device is disposed in a third channel, wherein each of the first channel, the second channel, and the third channel is separated from the respective lumens by an expandable divider.

12. The system of claim 11, wherein the first and second illumination devices include light sources.

13. The system of claim 11, wherein the first and second illumination devices include light guide tubes having light sources at proximal ends of the light guide tubes.

14. The system of claim 11, wherein the imaging and illumination devices are fixedly embedded within the thickness of material.

15. The system for claim 11, wherein the imaging and illumination devices are slidably received within the thickness of material.

16. The system of claim 11, wherein the divider is configured to collapse so as to not protrude into the respective lumens when the imaging and illumination devices are removed from the respective channels.

17. The system of claim 11, wherein each of the two lumens are axially fixed with respect the elongate member.

* * * * *